United States Patent [19]

Schmid

[11] Patent Number: 5,024,227
[45] Date of Patent: Jun. 18, 1991

[54] BIOELECTRICAL ELECTRODE

[75] Inventor: Walter Schmid, Pfaffenhofen, Fed. Rep. of Germany

[73] Assignee: ARBO Medizin-Technologie GmbH, Braunschweig, Fed. Rep. of Germany

[21] Appl. No.: 188,753

[22] Filed: Apr. 29, 1988

Related U.S. Application Data

[63] Continuation of Ser. No. 930,308, filed as PCT EP86/00103 on Feb. 27, 1986, published as WO86/05083 on Sept. 12, 1986, abandoned.

[30] Foreign Application Priority Data

Mar. 1, 1985 [DE] Fed. Rep. of Germany ....... 3507301

[51] Int. Cl.$^5$ ................................................ A61B 5/04
[52] U.S. Cl. .................................... 128/640; 128/641; 128/798; 128/802
[58] Field of Search ................................ 128/639–641, 128/798, 802, 803, 303, 13; 606/32

[56] References Cited

U.S. PATENT DOCUMENTS

| | | | |
|---|---|---|---|
| 3,993,049 | 11/1976 | Kater | 128/640 |
| 4,066,078 | 1/1978 | Berg | 128/640 |
| 4,125,110 | 11/1978 | Hymes | 128/64 |
| 4,161,174 | 7/1979 | Mercuri | 128/641 |
| 4,237,886 | 12/1980 | Sakurada et al. | 128/303.13 |
| 4,352,359 | 10/1982 | Larimore et al. | 128/640 |
| 4,362,165 | 12/1982 | Carmon et al. | 128/640 |
| 4,367,755 | 1/1983 | Bailey | 128/802 X |
| 4,458,696 | 7/1984 | Larimore | 128/798 |
| 4,474,570 | 10/1984 | Arivra et al. | 128/798 X |
| 4,554,924 | 11/1985 | Engel | 128/640 |

FOREIGN PATENT DOCUMENTS

| | | |
|---|---|---|
| 1144606 | 4/1983 | Canada . |
| 0085327 | 8/1983 | European Pat. Off. . |
| 0096330 | 12/1983 | European Pat. Off. . |
| 0115778 | 8/1984 | European Pat. Off. . |
| 2727396 | 12/1978 | Fed. Rep. of Germany ...... 128/640 |
| 3136193 | 4/1983 | Fed. Rep. of Germany . |
| 2464078 | 3/1981 | France . |

OTHER PUBLICATIONS

NASA Tech Brief, Nov. 1969, Brief No. 69-10598.

Primary Examiner—Lee S. Cohen
Attorney, Agent, or Firm—Foley & Lardner

[57] ABSTRACT

A bioelectrical electrode is disclosed consisting of metal on its skin-side contact surface and having a conductive adhesive layer covering at least part of the skin-side contact surface. The conductive adhesive layer is formed as a layer of an aqueous dispersion adhesive that is pressure-sensitive and contains a substance that dissociates in aqueous solution. The preferred adhesive layer comprises an aqueous dispersion of a thermoplastic acrylic resin and gelatin. The preferred dissociating substance is $MgCl_2$ and the preferred metal contact surface is zinc. The adhesive layer may additionally contain citric acid.

35 Claims, 1 Drawing Sheet

BIOELECTRICAL ELECTRODE

This application is a continuation of application Ser. No. 930,308, filed as PCT EP86/00103 on Feb. 27, 1986, published as WO86/05083 on Sept. 12, 1986 now abandoned.

BACKGROUND OF THE INVENTION

The invention relates to a bioelectrical electrode with an electrode body consisting of metal at least on its housing-side (i.e.—skin-side) contact surface and with a conductive adhesive layer covering at least the part of the housing-side contact surface.

DE-C-No. 3,156,193 has disclosed a disposable electrode for electromedical purposes, in particular for recording electrocardiograms, wherein a composite film with a silver/silver chloride composite layer on the skin side is provided in the orifice of an annular disk of foamed adhesive film. The skin-side contact surface of the composite film is coated with an electrically conductive gel or a conductive adhesive. Details of the conductive adhesive are not mentioned.

SUMMARY OF THE INVENTION

It is the object of the invention to provide a bioelectrical electrode which can be used in particular as a disposable electrode and which is prepared ready for use and, due to its construction, does not tend to produce artifacts, or to only a very small extent Starting from the bioelectrical electrode explained at the outset, this object is achieved according to the invention when the conductive adhesive layer is formed as a layer of aqueous dispersion adhesive having the property of being pressure-sensitive and contains a substance which dissociates in aqueous solution. The layer of dispersion adhesive is sufficiently tough to enable the contact surface to be fixed undisplaceably to the skin of the patient. The tendency of the electrode to produce artifacts is thus considerably reduced. The dissociating substance, which especially represents metal halides, in particular alkali halides or alkaline earth metal halides, preferably magnesium chloride, is dissolved in the layer of dispersion adhesive and acts as an ion-conductive electrolyte.

The layer of dispersion adhesive can be an aqueous dispersion of an acrylate ester copolymer which carries carboxyl groups and which may contain acrylonitrile. Aqueous dispersions of a thermoplastic acrylic resin, for example 2-ethylhexyl acrylate, or aqueous dispersions of cold-crosslinkable polyurethane elastomers, especially high-molecular elastomers, are also suitable.

In addition to the tacky dispersion substances discussed above, the layer of dispersion adhesive can also contain agents which increase surface tackiness. Polyvinylpyrrolidone, polyvinyl isobutyl ether, polyvinyl methyl ether, terpene resin and polyvinyl alcohol have proved to be suitable.

The layer of dispersion adhesive can contain conventional thickeners and/or binders such as, for example, gelatine, cellulose derivatives, polyisobutylene, glycerol or a vegetable gum. Gelatine is especially advantageous, since gelatine liquefies due to the body temperature, when the electrode has been stuck to the skin of the patient, and the conductivity of the dissociating substance is thus improved. Because of its hygroscopic properties, glycerol improves the resistance of the layer of dispersion adhesive to moisture. Other hygroscopic agents, for example 1,3-butanediol, propylene glycol or propylene carbonate, can also be used with advantage.

The dissociating substance is a dissociating metal salt, in particular a halide. The metal of the metal salt can be the metal of which the skin-contact surface of the electrode body consists. The skin-contact surface can consist in a known manner of silver, the layer of dispersion adhesive advantageously containing silver chloride or silver iodide. If other metals are used for cost reasons, the layer of dispersion adhesive preferably contains a complex former if the metal of the dissociating salt differs from the metal of the skin-contact surface. The complex former stabilizes the equilibrium of the dissociating system formed in this way and reduces the offset potential of the electrode. Citric acid and an alkylenediaminetetraacetic acid have proved to be suitable as complex formers in conjunction with alkali metal halides or rare metal halides, but in particular alkaline earth metal halides. These substances are particularly suitable for skin-contact surfaces of zinc with layers of dispersion adhesive containing $MgCl_2$.

In a preferred embodiment, the layer of dispersion adhesive contains 30 to 80 weight units of an aqueous dispersion of a thermoplastic acrylic resin and/or an acrylate ester copolymer carrying carboxyl groups and/or a polyurethane elastomer, the solids content of the dispersion being preferably between 40 and 70 percent. The layer of dispersion adhesive also contains preferably between about 5.2 and 43 weight units of the metal halide which dissociates in aqueous solution, about 1.2 to 35 weight units of gelatine having a jelly strength of preferably between 100 and 300 Bloom, and 2.4 to 52 weight units of glycerol. As complex formers, about 0.3 to 4.3 weight units of citric acid and, if appropriate, additionally an alkylenediaminetetraacetic acid in a quantity of preferably about 0.1 to 0.3 weight units can have been added, in particular if MgCl is present as the dissociating substance and the skin-contact surface of the electrode body consists of zinc. To improve the constancy of moisture content, about 0.2 to 26.4 weight units of propylene glycol and/or about 0.2 to 12.9 weight units of 1,3-butanediol can have been added as hygroscopic agents. To improve the surface tackiness, about 0.8 to 16 weight units of polyvinylpyrrolidone and, if appropriate, additionally about 3.5 to 10.5 weight units of polyvinyl methyl ether and/or about 1.3 to 4 weight units of polyvinyl isobutyl ether have been found to be suitable. Finally, it should be mentioned that, in the preparation of the layer of dispersion adhesive, thickening can be accelerated by an addition of about 1 to 5 weight units of triethanolamine.

The skin-contact surface of the electrode body of the electrode according to the invention consists preferably of zinc. The use of zinc as an electrode material is known. However, it has been found, surprisingly, that the offset potential behavior and the stability of the electrode can be substantially improved if the skin-contact surface is formed by a hot-spray galvanized zinc layer, in particular with a grainy surface structure. The zinc melted in the flame is atomized by an air jet and blown onto the electrode body. It has been found that hot-spray galvanized zinc surfaces are less susceptible to oxidation than zinc surfaces formed by other processes. In addition, the grainy structure of the hot-spray galvanized zinc surface enlarges the surface area which is in contact with the layer of dispersion adhesive or another electrolyte layer. Electrodes with a skin-contact surface of hot-spray galvanized zinc can therefore also be used in conjunction with non-adhesive electrolyte layers, preferably electrolyte layers stabilized with complex formers of the above type.

To improve adhesion of the hot-spray galvanized zinc layer to the electrode body, the latter is preferably roughened, in particular by sandblasting, before the zinc layer is applied.

The electrode body consists preferably of a flexible plastic film piece, in particular of electrically conductive plastic material, for example of polycarbonate. A pin molded to the film piece or a metal connecting knob fixed in contact with the electrically conductive film side away from the skin can be provided as the connecting element. If the film is thermoplastically deformable, a bead in the shape of a knob and, if appropriate, filled by a stiff material can have been embossed into the film. The layer of dispersion adhesive applied to the zinc surface is covered by silicone paper or detachable plastic film, for example of polyethylene, in order to prevent drying out of the layer of dispersion adhesive. The side, away from the skin, of the electrically conductive film piece forming the electrode body is covered by an insulating film, for example of PVC, with the exception of the connecting element. In addition, to enlarge the adhesive area, the electrode body can have been inserted into the orifice of a pressure-sensitive adhesive annular disk of foamed plastic.

Illustrative examples of the invention will be explained below in more detail by reference to drawings in which:

DESCRIPTION OF THE PREFERRED EMBODIMENTS

Figure 1:
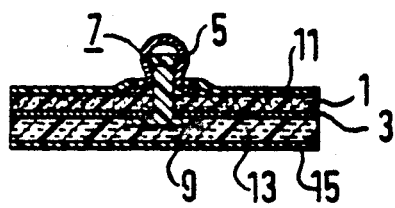
FIGS. 1 to 3 show cross-sections through three different embodiments of bioelectrical electrodes.

The electrode of FIG. 1 comprises an essentially flat film piece 1 of an electrically conductive, flexible plastic material which carries a zinc layer 3 on the side which in use faces the skin of the patient. A metal connecting knob 5, which is fixed to the film piece 1 by means of a plastic component 7 consisting of an insulating material, bears against the side of the film piece 1, away from the skin. The plastic component 7 penetrates the film piece 1 and a head 9 grips behind the film piece 1 on the side away from the metal connecting knob 5. With the exception of the metal connecting knob 5, the side of the film piece 1, away from the skin, is covered by an insulating film 11, for example a PVC film. A layer 13 of an aqueous dispersion adhesive, explained in more detail below, is applied to the skin side of the zinc layer 3. The layer 13 of dispersion adhesive has the properties of a pressure-sensitive adhesive and contains a metal salt, which is explained in more detail below and dissociates in aqueous solution, in particular a halide. The skin side of the layer 13 of the dispersion adhesive is covered in the usual way with a silicone paper 15 which can be removed for use.

Figure 2:
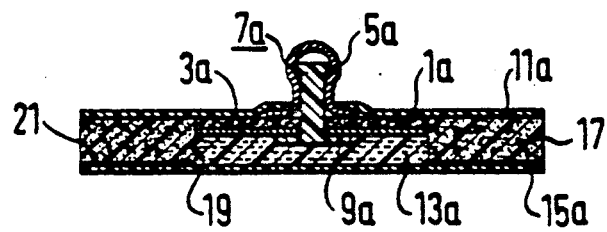

FIG. 2 shows another embodiment of a bioelectrical electrode. Parts having the same action are designated in FIG. 2 by the reference numbers of FIG. 1 and, to distinguish them, are provided with the letter a. For an explanation of these parts, reference is made to the description of FIG. 1. The electrode of FIG. 2 differs essentially only by a flexible annular disk 17 which consists of an insulating foamed plastic material and in the orifice 19 of which the film piece 1a including the layer 13a of dispersion adhesive is located. The film piece 1a is fixed to the surface, away from the skin, of the annular disk 17 by means of the insulating film 11a reaching over the latter. On its skin side, the annular disk 17 is provided with a layer 21 of pressure-sensitive adhesive, the silicone paper 15a also releasably covering the layer 21 of the pressure-sensitive adhesive. The annular disk 17 improves adhesion of the electrode to the skin of the patient.

Figure 3:
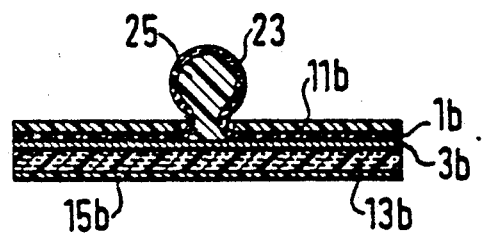

FIG. 3 shows a further embodiment of a bioelectrical electrode. Parts having the same action are provided in FIG. 3 with the reference numbers of FIG. 1 and, for distinguishing them, additionally with the letter b. To explain the mode of action, reference is made to the description of FIG. 1. The electrode of FIG. 3 differs from the electrode of FIG. 1 essentially only in the shaping of its connecting knob which is made in the form of a bead 23 which curves into the film piece 1b towards the side away from the skin and serves as the connecting knob. In order to enable the bead 23 to be molded in, the film piece 1b consists of electrically conductive, thermoplastic material. The interior of the bead 23 is stiffened with a plastic part 25, consisting in particular of a thermosetting plastic material.

Figure 4:
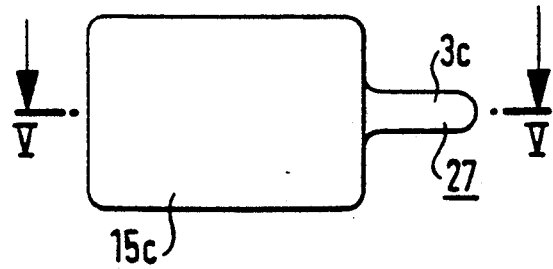
FIG. 4 shows a plan view of a fourth embodiment of a bioelectrical electrode and FIG. 5 shows a cross-section through the electrode of FIG. 4, as viewed along a line V—V.
Figure 5:
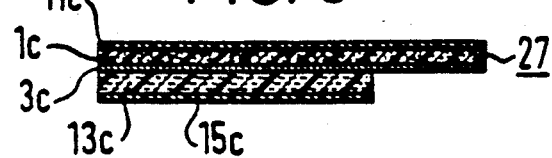

FIGS. 4 and 5 show a further variant of a bioelectrical electrode. Parts having the same action are designated in FIGS. 4 and 5 with the reference numbers of FIG. 1 and additionally with the letter c. For explanation, reference is made to the description of FIG. 1. The electrode differs from the electrode of FIG. 1 essentially only in the shaping of the connecting element which is formed as a connecting pin 27 integrally molded to the film piece 1c. The zinc layer 3c extends also across the connecting pin 27. In the illustrative example shown, the insulating film 11c likewise extends across the connecting pin 27c. However, the region of the connecting pin 27c can also be exposed. The insulating film 11c can be completely omitted if, and this can be provided as an alternative, the film piece 1c consists of a non-conductive plastic material.

The zinc layers 3, 3a, 3b and 3c of the electrodes discussed above consist of substantially pure zinc applied by the hot-spray process. Such processes are known. For example, the zinc in the form of wire is incipiently melted in a burner flame and is atomized and sprayed onto the film piece by an air stream supplied via a nozzle. Grainy and hence enlarged surface is thus obtained. Surprisingly, it has been found that a zinc layer applied in this way is less susceptible to oxidation and hence makes possible electrodes with a lower transition resistance and a better offset potential behavior.

In a first preferred embodiment, the layer 13, 13a, 13b or 13c of dispersion adhesive contains 30 to 80 weight units of an aqueous dispersion of a thermoplastic acrylic resin of about 60 percent dry content, for example 2-ethylhexyl acrylate,
5.2 to 43 weight units of magnesium chloride,
0.31 to 4.3 weight units of citric acid,
0.8 to 4 weight units of polyvinylpyrrolidone,
2.4 to 52 weight units of glycerol,
1.2 to 35 weight units of gelatine having a jelly strength from 100 to 300 Bloom
2 to 5 weight units of triethanolamine,
5 to 15 weight units of vegetable gum,
0.2 to 12.9 weight units of 1,3-butanediol and 0.2 to 6.45 weight units of propylene glycol.

To prepare such an electrolytically conductive dispersion adhesive material, a solution number 1 is prepared from 30 to 80, for example about 50, weight units of distilled water, 60 to 120, for example about 80, weight units of glycerol, 5 to 30, for example about 20, weight units of 1,3-butanediol, 5 to 15, for example about 10, weight units of propylene glycol, 5 to +, for example about 10, weight units of magnesium chloride, 0.3 to 3, for example about 0.5, weight units of citric acid and 30 to 80, for example about 60, weight units of gelatine having a jelly strength of 100 to 300, for example about 200 Bloom.

Moreover, a solution number 2 is prepared from 30 to 80, for example about 50, weight units of an aqueous dispersion of a thermoplastic acrylic resin of about 60 percent dry content, for example Plextol E 220 from Messrs. Röhm GmbH, Darmstadt, 5 to 30, for example about 10, weight units of magnesium chloride, 0.3 to 3, for example about 0.5, weight units of citric acid, 2 to 10, for example about 3, weight units of polyvinylpyrrolidone solution in water or alcohol in a weight ratio of 40:100, 2 to 5, for example about 4, weight units of triethanolamine, and 5 to 15, for example about 10, weight units of vegetable gum.

After initial swelling, the solution number 1 is dissolved by heating in a water bath. 15 to 45 weight units of solution number 1 are stirred into solution number 2. The mixture of the solutions 1 and 2 is cast to give a layer or processed on a laminating machine to give uniform thickness. After evaporation of the solvents, if necessary accelerated by heat, the layer of dispersion adhesive is applied to the zinc layer of the electrode. Alternatively, the layer of dispersion adhesive can also be prepared directly on the zinc layer.

In a second preferred embodiment, the layer 13, 15a, 13b or 13c of dispersion adhesive contains 30 to 80 weight units of an aqueous dispersion of a cold-crosslinkable acrylate ester copolymer carrying carboxyl groups, having a solids content of about 50 percent,
3.5 to 10.5 weight units of polyvinyl methyl ether,
4 to 16 weight units of polyvinylpyrrolidone,
1.3 to 4 weight units of polyvinyl isobutyl ether,
5.2 to 43 weight units of magnesium chloride,
0.31 to 4.3 weight units of citric acid,
1.2 to 0.3 weight units of ethylenediaminetetraacetic acid,
1 to 3 weight units of triethanolamine,
5.2 to 26.45 weight units of propylene glycol,
2.4 to 52 weight units of glycerol,
0.2 to 12.9 weight units of propylene glycol and
1.2 to 35 weight units of gelatine having a jelly strength of 100 to 300 Bloom.

To prepare such a dispersion adhesive material, a solution number 3 is prepared, consisting of 30 to 80, for example about 40, weight units of an aqueous dispersion of a cold-crosslinkable copolymer carrying carboxyl groups and based on acrylate esters and concurrent use of acrylonitrile, having a solids content of about 50 percent, for example obtainable as Acronal 80 D, about 50 percent, from Messrs. BASF, 5 to 15, for example about 10, weight units of a solution of polyvinyl methyl ether in water with a water content of 70 percent by weight, 10 to 40, for example about 30, weight units of a solution of polyvinylpyrrolidone in alcohol at a mixing ration of 40:100 percent by weight, 2 to 6, for example about 3, weight units of a dispersion of polyvinyl isobutyl ether in water at a mixing ration of 40:60 percent by weight, 5 to 30 for example about 10, weight units of magnesium chloride, 0.3 to 5, for example about 0.5, weight units of citric acid, 0.1 to 0.3, for example about 0.1, weight units of ethylenediaminetetraacetic acid, 1 to 5, for example about 3, weight units of triethanolamine and 5 to 20, for example about 15, weight units of propylene glycol.

The swollen solution number 1 is dissolved by heating a water bath. 15 to 45 weight units of solution number 1 are added to solution number 3 with constant stirring. The mixture is cast to give a layer or processed on a laminating machine to give uniform thickness. After drying, the layer of dispersion adhesive is applied to the zinc layer. Alternatively, the layer of dispersion adhesive can again be prepared directly on the zinc layer.

A part of the gelatine can be replaced by polyisobutylene and/or cellulose derivatives. Gelatine improves the conductivity of the electrode, since it slightly softens by body temperature. Polyvinylpyrrolidone improves not only the surface tackiness of the layer of dispersion adhesive but, due to its hygroscopic behavior, releases moisture on the skin. Furthermore, polyvinylpyrrolidone reduces any possible irritant effect of the electrolyte.

I claim:

1. A bioelectrical electrode, with an electrode body (1) consisting of metal at least on its skin-side contact surface and with a conductive adhesive layer (13) covering at least part of the skin-side contact surface, (3), wherein the conductive adhesive layer is formed as a layer (13) of an aqueous dispersion adhesive having the property of being pressure-sensitive and containing a substance which dissociates in aqueous solution wherein said adhesive comprises an aqueous dispersion of a thermoplastic acrylic resin and gelatin.

2. The electrode as claimed in claim 1, wherein the layer (13) of dispersion adhesive additionally comprises at least one agent which increases surface tackiness selected from the group consisting of, a dispersion of a polyvinyl isobutyl ether, polyvinyl methyl ether and terpene resin.

3. The electrode as claimed in claim 1, wherein the layer (13) of dispersion adhesive additionally comprises at least one of a thickener and a binder.

4. The electrode as claimed in claim 1, wherein the layer (13) of dispersion adhesive comprises dissolved hygroscopic agents selected from the group consisting of glycerol, 1,3-butanediol, propylene glycol and propylene carbonate.

5. The electrode as claimed in claim 1, wherein the dissociating substance contains, as the main constituent, a salt of a metal which differs from the metal of the contact surface, and wherein the layer (13) of dispersion adhesive contains a complex former for stabilizing the equilibrium.

6. The electrode as claimed in claim 5, wherein the layer (13) of dispersion adhesive comprises a salt selected from the group consisting of an alkali metal halide, an alkaline earth metal halide and a rare metal halide and a complex former selected from the group consisting of citric acid and alkylenediaminetetraacetic acid.

7. The electrode as claimed in claim 6, wherein the layer (13) of dispersion adhesive comprises halide and citric acid in a weight ration of 15:1 to 40:1.

8. The electrode as claimed in claim 6, wherein the layer (13) of dispersion adhesive contains the halide and alkylenediaminetetraacetic acid in a weight ration of about 30:1.

9. The electrode as claimed in claim 5 wherein the contact surface consists essentially of An and the dissociating substance consists essentially of $MgCl_2$.

10. The electrode as claimed in claim 1, wherein the layer (13) of dispersion adhesive contains 30 to 80 weight units of an aqueous dispersion of a thermoplastic acrylic resin, 5.2 to 43 weight units of a metal halide, 1.2 to 35 weight units of gelatine (Bloom 100 to 300), and 2.4 to 52 weight units of glycerol.

11. The electrode as claimed in claim 10, wherein the layer (13) of dispersion adhesive contains a halide of a metal other than that of the contact surface.

12. The electrode as claimed in claim 11, wherein the halide of a metal is $MgCl_2$ and the conductive adhesive layer additionally comprises about 0.3 to 4.3 weight units of citric acid.

13. The electrode as claimed in claim 10, wherein the layer (13) of dispersion adhesive contains 0.2 to 26.45 weight units of propylene glycol.

14. The electrode as claimed in claim 13, wherein the layer (13) of dispersion adhesive contains 0.2 to 12.9 weight units of 1,3-butanediol.

15. The electrode as claimed in claim 10, wherein the layer (13) of dispersion adhesive contains 1 to 5 weight units of triethanolamine.

16. The electrode as claimed in claim 1, wherein the skin-contact surface comprises a hot-spray galvanized zinc layer (3).

17. The electrode as claimed in claim 16, wherein the skin-contact surface has a grainy surface structure.

18. The electrode as claimed in claim 16, wherein the surface of the electrode body under the skin-contact surface is rough.

19. The electrode as claimed in claim 16, wherein the electrode body comprises an essentially two-dimensional, flexible plastic film piece (1) having the zinc layer (3) on one of its two surfaces.

20. The electrode as claimed in claim 19, wherein the film piece (1) consists of an electrically conductive plastic film.

21. The electrode as claimed in claim 20, wherein, on the film piece (1;1a) side away from the skin, a metal connecting knob (5;5a) is provided which is held in electric contact with the film piece (1;1a) on the latter by means of a fixing component (7;7I) which consists of an insulating plastic and penetrates through an orifice in the film piece (1;1a).

22. The electrode as claimed in claim 21, wherein, on the film piece (1;1a;1b) surface away from the skin is covered with an insulating film (11;11a; 11b), with the exception of the connecting knob (5; 5a;23).

23. The electrode as claimed in claim 22, wherein a flexible annular disk (17), carrying a layer (21) of pressure-sensitive adhesive on its skin-side surface, is fixed to the skin-side surface of the film piece (1a) forming the skin-contact surface and/or of a region of the insulating film (11a) extending beyond this film piece (1a), and wherein the layer (5a) of dispersion adhesive fills the interior of the annular disk (17).

24. The electrode as claimed in claim 23, wherein the flexible annular disk is a foamed plastic material.

25. The electrode as claimed in claim 22, wherein the insulating film is PVC material.

26. The electrode as claimed in claim 20, wherein the film piece (1b) consists of a thermoplastic material, and wherein a bead (23), the interior of which contains a plastic body (25) which stiffens the bead (23) is integrally molded into the film piece (1b) in order to form a connecting knob protruding beyond the film piece (1b) surface away from the skin.

27. The electrode as claimed in claim 26, wherein the plastic body consists of a thermosetting plastic.

28. The electrode as claimed in claim 19, wherein the film piece (1c) merges integrally into a connecting pin (27).

29. The electrode as claimed in claim 1, wherein said adhesive comprises an aqueous dispersion of a polyacrylate ester polymer.

30. The electrode as claimed in claim 1, wherein said adhesive comprises 2-ethylhexyl acrylate.

31. The electrode as claimed in claim 1, wherein the conductive adhesive layer consists essentially of the aqueous dispersion of thermoplastic acrylic resin, the dissociating substance and gelatin.

32. A bioelectrical electrode, with an electrode body consisting of metal at least on its skin-side contact surface and having a conductive adhesive layer covering at least part of the skin-side contact surface, wherein the conductive adhesive layer consists essentially of an aqueous dispersion adhesive that is pressure-sensitive, a substance that dissociates in aqueous solution, and gelatin, said electrode formed by the steps of:

preparing a heated solution of gelatin and an aqueous dispersion of a thermoplastic acrylic resin, at least one of said solution and said aqueous dispersion comprising the substance that dissociates in aqueous solution;

mixing the solution of gelatin with the aqueous dispersion of thermoplastic resin to form a conductive adhesive; and forming an layer of the conductive adhesive on the skin-side contact surface.

33. An electrode as claimed in claim 32, wherein the substance that dissociates in aqueous solution comprises $MgCl_2$.

34. An electrode as claimed in claim 33, wherein the skin-side contact surface of the electrode comprises a galvanized zinc layer formed by hot-spraying.

35. An electrode as claimed in claim 34, wherein the layer of conductive adhesive additionally comprises citric acid.

* * * * *